(12) United States Patent
Lynch (10) Patent No.: US 9,720,256 B2
(45) Date of Patent: Aug. 1, 2017

(54) GOGGLES WITH INTEGRAL CLEANING MECHANISM

(71) Applicant: Jeffrey Allen Lynch, Gig Harbor, WA (US)

(72) Inventor: Jeffrey Allen Lynch, Gig Harbor, WA (US)

( * ) Notice: Subject to any disclaimer, the term of this patent is extended or adjusted under 35 U.S.C. 154(b) by 0 days.

(21) Appl. No.: 15/081,538

(22) Filed: Mar. 25, 2016

(65) Prior Publication Data

US 2016/0223841 A1    Aug. 4, 2016

Related U.S. Application Data

(63) Continuation-in-part of application No. 13/523,268, filed on Jun. 14, 2012, now Pat. No. 9,323,076.

(60) Provisional application No. 61/523,541, filed on Aug. 15, 2011.

(51) Int. Cl.
*G02C 11/08* (2006.01)
*G02C 13/00* (2006.01)
*A61F 9/02* (2006.01)

(52) U.S. Cl.
CPC .............. *G02C 11/08* (2013.01); *A61F 9/027* (2013.01); *G02C 13/006* (2013.01)

(58) Field of Classification Search
None
See application file for complete search history.

(56) References Cited

U.S. PATENT DOCUMENTS

| | | | |
|---|---|---|---|
| 3,647,059 A | 3/1972 | Humphreys | |
| 4,342,128 A | 8/1982 | Doyle | |
| 6,131,209 A | 10/2000 | Thayer et al. | |
| 6,881,273 B1 | 4/2005 | Oberman | |
| 2006/0059608 A1* | 3/2006 | Difilippo | A61F 9/028 2/436 |
| 2006/0177227 A1 | 8/2006 | Blasko et al. | |
| 2008/0000432 A1 | 1/2008 | Alhegelan | |
| 2013/0239990 A1* | 9/2013 | Lynch | G02C 11/08 134/6 |

* cited by examiner

*Primary Examiner* — Nicole Blan
(74) *Attorney, Agent, or Firm* — Eric Karich; Karich & Associates (57) ABSTRACT

Goggles include a lens mounted on a frame having a gasket adapted for seating against a user's face. A strap is attached to the frame for securing the goggles around the user's head. The goggles include a retraction mechanism fixedly mounted on the frame or the strap, a squeegee for cleaning the lens of the goggles, and a cord having a proximal end and a distal end, the proximal end being attached to the squeegee, and the distal end being operably attached to the retraction mechanism.

6 Claims, 7 Drawing Sheets

GOGGLES WITH INTEGRAL CLEANING MECHANISM

CROSS-REFERENCE TO RELATED APPLICATIONS

This application for a utility patent is a continuation-in-part of application Ser. No. 13/523,268, filed Jun. 14, 2012, which claims the benefit of U.S. Provisional Application No. 61/523,541, filed Aug. 15, 2011.

BACKGROUND OF THE INVENTION

Field of the Invention

This invention relates generally to goggles, and more particularly to a squeegee device for wiping moisture from the goggles while the user is wearing the goggles.

Description of the Related Art

The prior art teaches a wide range of devices for wiping and cleaning goggles, such as while skiing, snowboarding, riding motorcycles and snow machines, or engaged in similar outdoor activities. In one example, Doyle, U.S. Pat. No. 4,342,128, teaches a squeegee that is operably attached to a cord that may be worn around the neck in the form of a necklace. While the squeegee is useful for cleaning goggles, the attachment strap used is not well suited for use while engaged in outdoor physical activities, since the squeegee may be difficult to locate and grasp while engaged in the activity, especially if wearing gloves. Furthermore, the necklace cord upon which it is attached may pose a safety danger if it snags on surrounding objects (e.g., a ski lift, trees, etc.).

The prior art also teaches various devices for cleaning other forms of eyewear, including a wide range of cloths and similar products for wiping moisture, dirt, and other matter from the eyewear. Oberman, U.S. Pat . No. 6,881,273, for example, teaches an eyewear cleaning device that includes a housing, a retractable cord, and a soft, nonabrasive cloth mounted on the cord for cleaning eyewear lenses. The housing is mounted on a wall or similar structure, and may further include a cleaning fluid dispenser. The device can be attached to clothing or related items (e.g., a backpack) with a variety of hooks or clips, or the device may be attached to a support structure (e.g., a wall) with an adhesive or similar attachment means.

Thayer et al., U.S. Pat. No. 6,131,209, teaches an eyewear cleaning apparatus which utilizes a flexible retaining band that has ends which engage and retain eyewear such as eyeglasses, sunglasses, goggles and the like to allow the eyewear to be carried about the neck of the user. A selectively closeable compartment is positioned on the band intermediate the ends and contains a specialized lens cleaning cloth which is moveable between an extended cleaning position confronting the lenses of the eyewear and a rolled or folded storage position within the compartment where the cloth can be effectively carried, stored and protected from contamination yet always be available for lens cleaning when needed. When in the stored position, the cloth is substantially undetectable to the casual eye, and the band retains its aesthetically attractive appearance.

While the prior art teaches a wide variety of eyewear cleaning devices, the prior art does not teach ski goggles that include a retraction mechanism integrally mounted on the ski goggles, and a squeegee that is attached to the retraction mechanism via a cord that enables the squeegee to be retracted in a manner that does not interfere with the user's activities. The prior art also does not teach a cleaning device that is adapted to be used while the user is actively engaged in an athletic activity. The present invention fulfills these needs and provides further related advantages as described in the following summary.

SUMMARY OF THE INVENTION

The present invention teaches certain benefits in construction and use which give rise to the objectives described below.

The present invention provides goggles with an integral cleaning system. The goggles include a lens mounted on a frame, the frame having a gasket adapted for seating against a user's face, and further comprising a strap adapted for securing the frame around the user's head. The goggles include a retraction mechanism fixedly mounted on the frame or the strap, a squeegee for cleaning the lens of the goggles, and a cord having a proximal end and a distal end, the proximal end being attached to the squeegee, and the distal end being operably attached to the retraction mechanism.

A primary objective of the present invention is to provide a goggles having advantages not taught by the prior art.

Another objective is to provide goggles that are mounted directly to the goggles so that the device may be used while the user is actively engaged in a sporting event, such as snowboarding, skiing, motocross, snowmobiling, paintball, and similar sports.

A further objective is to provide goggles that include a squeegee that is retractable and is held against the eyewear, so that the cleaning element may be returned to a stored position with minimal time, effort, or distraction following use.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings.

DETAILED DESCRIPTION OF THE INVENTION

The above-described drawing figures illustrate the invention, an eyewear cleaning device 10 that is used to clean goggles 12. The eyewear cleaning device 10 is adapted to be mounted on the eyewear 12, so that the user may clean the eyewear 12 while the eyewear 12 is being worn, even while the user is actively engaged in a sports activity.

Figure 1:
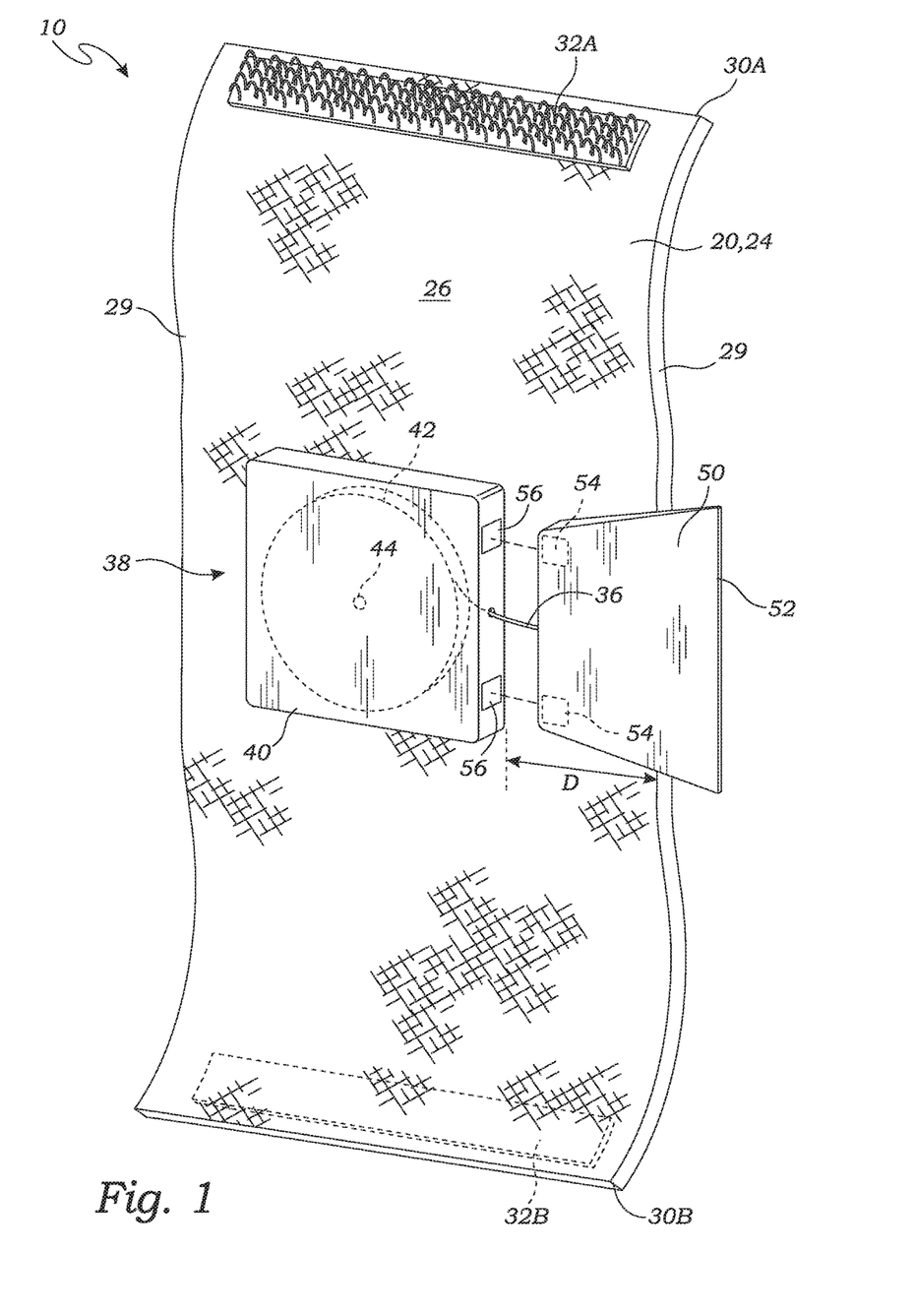
FIG. 1 is a perspective view of an eyewear cleaning device according to one embodiment of the present invention.
Figure 2:
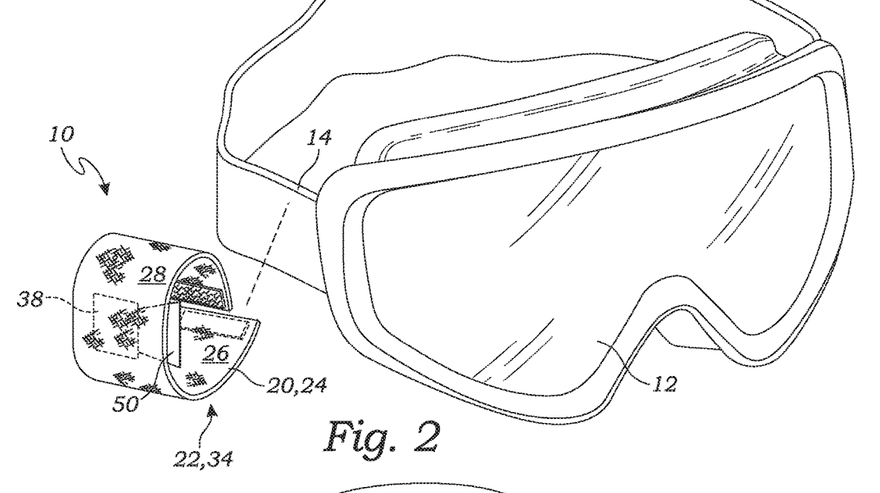
FIG. 2 is a perspective view of the eyewear cleaning device of FIG. 1 being mounted on a strap of a pair of goggles.

FIG. 1 is a perspective view of the eyewear cleaning device 10 according to one embodiment of the present invention. FIG. 2 is a perspective view of the eyewear cleaning device 10 of FIG. 1 being mounted on the eyewear 12. As shown in FIGS. 1 and 2, the eyewear cleaning device 10 is adapted to be mounted on the eyewear 12 for wiping moisture from the eyewear 12.

As illustrated in FIGS. 1 and 2, the eyewear cleaning device 10 includes a mounting element 20, a cord 36, and a squeegee 50. The mounting element 20 is adapted for mounting the eyewear cleaning device 10 on the eyewear 12. In this embodiment, the eyewear 12 is a pair of goggles 12, and the mounting element 20 is adapted to be mounted on a strap 14 of the goggles 12, which is flexible and elastic, and which holds the goggles 12 on the head of the user. While goggles 12 are illustrated herein, the eyewear cleaning device 10 may be mounted on other forms of eyewear (e.g., sunglasses, protective masks, etc.).

In the embodiment of FIGS. 1 and 2, the mounting element 20 includes a loop mounting system 22 that wraps around the strap 14 of the goggles 12 for securely mounting the eyewear cleaning device 10 on the goggles 12. The loop mounting system 22 may include a flexible body 24 having an inside surface 26, an outside surface 28, a pair of side edges 29, and a pair of opposed edges 30A and 30B. The flexible body 24 may be formed of a flexible material (e.g., Neoprene®, any form of fabric, or any other material known to those skilled in the art that is suitable for these purposes). In this embodiment, fasteners 32A and 32B are attached adjacent to the pair of opposed edges 30A and 30B so that the flexible body 24 may be wrapped around the strap 14 of the goggles 12 and connected to form a loop 34 for mounting the device on the goggles 12. The fasteners 32A and 32B may be hooks and loops fasteners (i.e., Velcro®), or any type of snaps, zippers, buttons, or other fasteners known in the art.

In an alternative embodiment, the mounting element 20 may include alternative structures known in the art for mounting the eyewear cleaning device 10 directly onto the goggles 12, including alternative snaps, hooks and loops fasteners, as well as other structures that mount the device to the goggles 12, either to the strap 14 as illustrated or directly to other parts of the goggles 12.

As illustrated in FIGS. 1 and 2, the cord 36 is attached to the mounting element 20 and the squeegee 50, for hanging the squeegee 50 on the mounting element 20. The cord 36 may be constructed of nylon or any other suitable material known in the art, and should be long enough to enable the squeegee 50 to be used to clean the goggles 12.

In the embodiment of FIGS. 1 and 2, the cord 36 is connected to the mounting element 20 via a retraction mechanism 38 that includes an outer housing 40 and a retractable reel 42 operably mounted within the outer housing 40. The retractable reel 42 may include a biasing element 44 (e.g., spring or other biasing structure) for biasing the retractable reel 42 towards a retracted position, illustrated in FIG. 2 Also illustrated in FIG. 2, the retraction mechanism 38 may be mounted a distance D from one of the side edges 29 of the flexible body 24, so that the squeegee 50 may at least partially recess into the loop 34 of the flexible body 24 when the eyewear cleaning device 10 is mounted on the strap 14 of the goggles 12.

Figure 3:
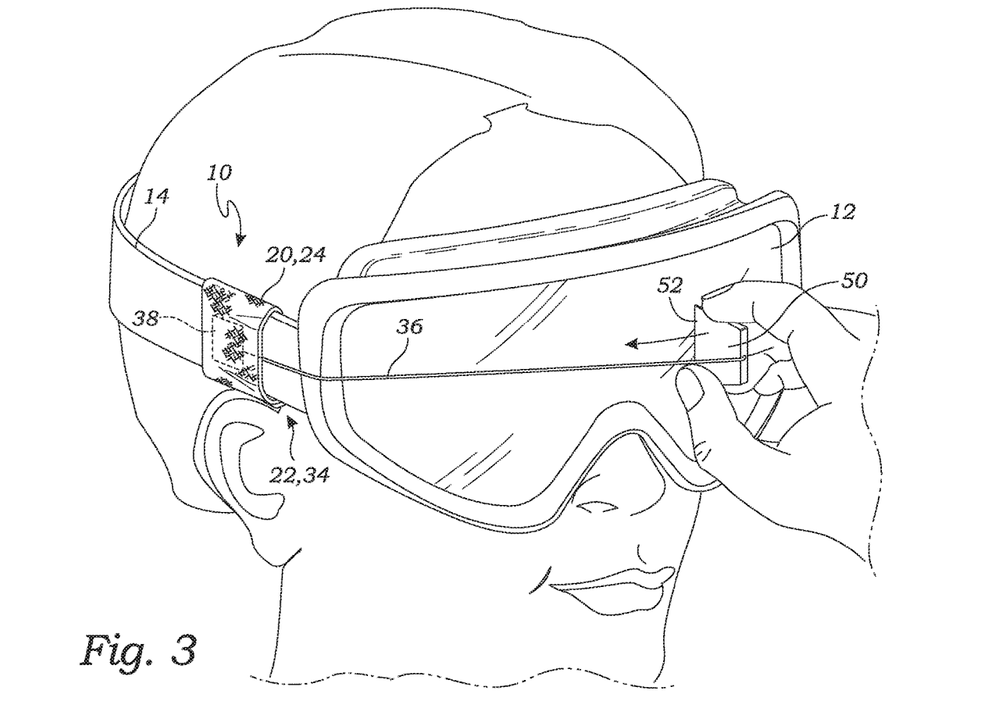
FIG. 3 is a perspective view of the eyewear cleaning device being used to clean the goggles.

FIG. 3 is a perspective view of the eyewear cleaning device 10 being used to clean the goggles 12. As illustrated in FIGS. 1-3, the squeegee 50 may be used for cleaning the pair of goggles 12, even while the goggles 12 are being worn, and even while the user is engaged in athletic activity (e.g., snowboarding, skiing, motocross, snowmobiling, paintball, etc.). In this embodiment, the squeegee 50 may include a cleaning edge 52 (e.g., rubber, plastic, or other suitable material known in the art) for wiping clean the goggles 12. The cleaning edge 52 may be any form of wiping device that is equivalent to a standard squeegee such as is known in the art. The term "rubber" in this element is hereby defined to include any form of rubber or similar or equivalent material, such as silicone or other suitable material known in the art.

In one embodiment, the squeegee 50 and the retraction mechanism 38 may further include mating surfaces shaped to engage each other to hold the squeegee 50 against the retraction mechanism 38. In one embodiment, the mating surfaces include magnets 54 and 56 (and/or metallic materials that are attracted to magnets) that magnetically hold the squeegee 50 against the outer housing 40, until the user removes the squeegee 50 from the outer housing 40 for use. In this embodiment, there are two magnets 54 in the squeegee 50 and two magnets 56 in the outer housing 40, and the magnetic attraction biases the squeegee 50 to the retracted position against the outer housing 40.

As illustrated in FIG. 3, once the flexible body 24 has been fastened around the strap 14 of the goggles 12, the eyewear cleaning device 10 is securely mounted on the goggles 12 and may be worn during physical activities (e.g., skiing, or other sports that utilize goggles 12 or other eyewear). The squeegee 50 is held securely against the flexible body 24 (and potentially partially within the loop 34 formed by the flexible body 24) by the cord 36, which is biased towards the retracted position, as described above.

When need arises, the user may grasp the squeegee 50 and pull it away from the strap 14 of the goggles 12, so that he or she can use the squeegee 50 to wipe the goggles 12 clean. When done cleaning the goggles 12, the user can simply release the squeegee 50, and the cord 36 functions to pull the squeegee 50 back into place, out of the way of the user.

Figure 4:
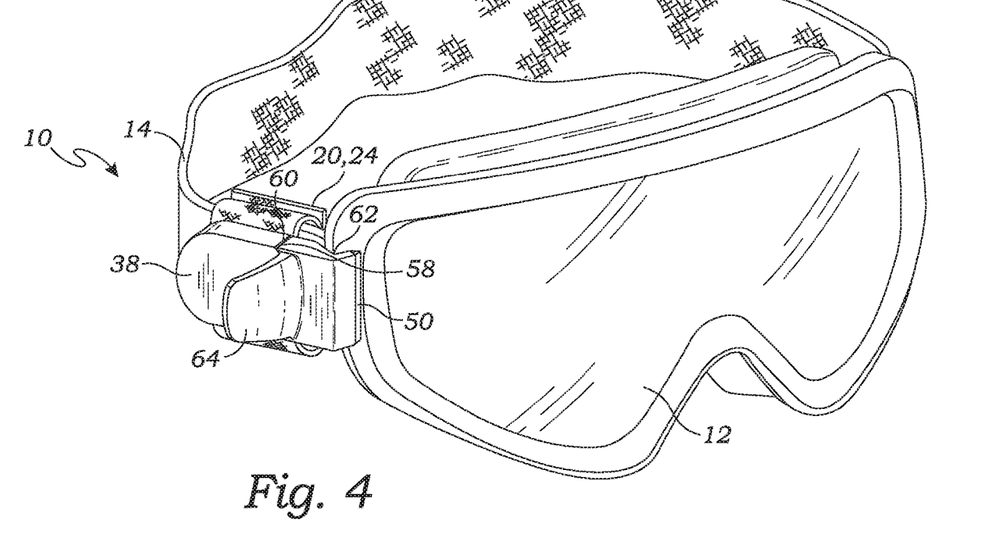
FIG. 4 is a perspective view of an alternative embodiment of the eyewear cleaning device, illustrating the eyewear cleaning device removably mounted on the goggles via a loop.
Figure 5:
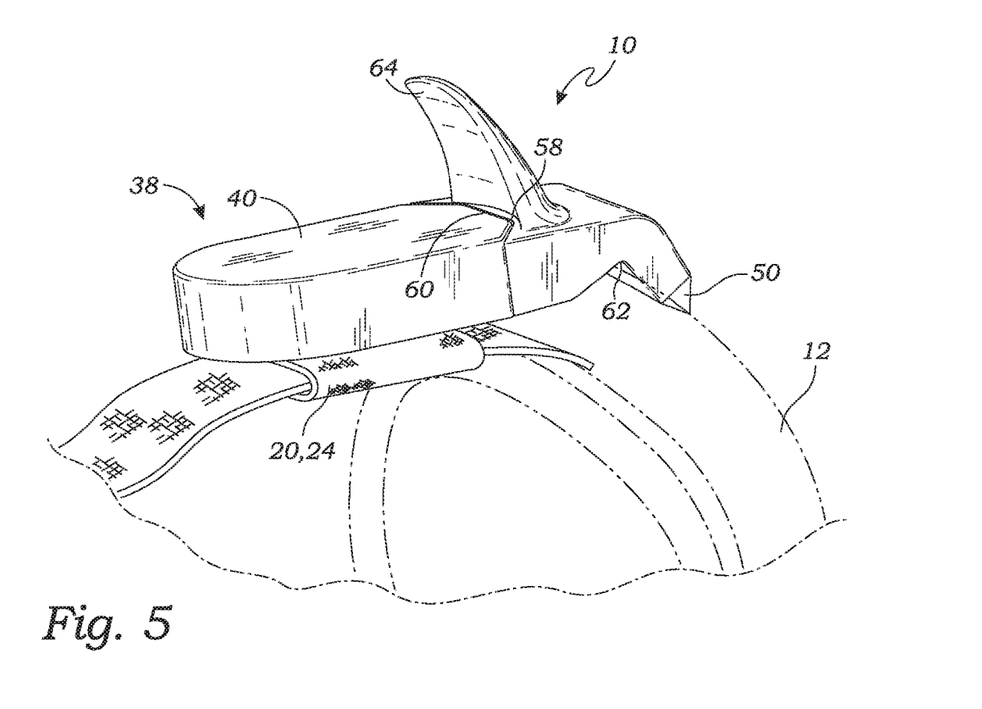
FIG. 5 is a bottom perspective view thereof.
Figure 6:
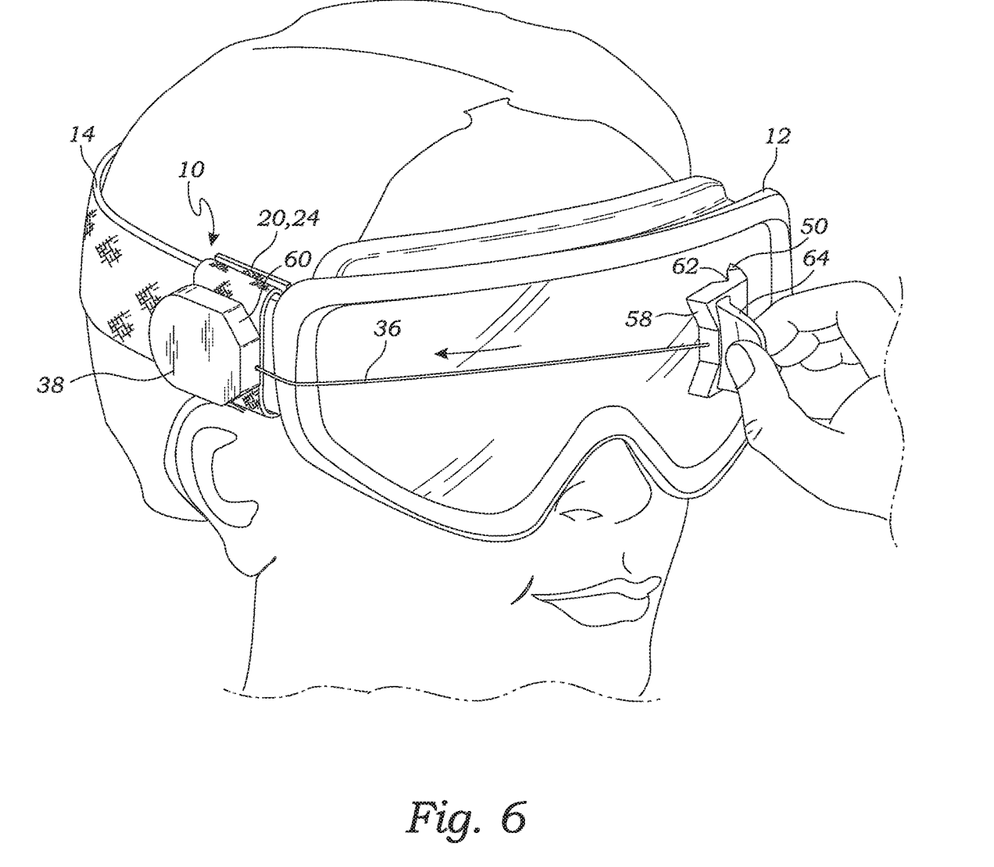
FIG. 6 is perspective view of the eyewear cleaning device of FIG. 4 being used to clean the goggles.

FIG. 4 is a perspective view of an alternative embodiment of the eyewear cleaning device 10. FIG. 5 is a bottom perspective view thereof. FIG. 6 is perspective view of the eyewear cleaning device 10 of FIG. 4 being used to clean the goggles 12. As shown in FIGS. 4-6, the squeegee 50 includes a first interlocking shaped surface 58, and the outer housing 40 includes a second interlocking shaped surface 60.

In the embodiment of FIGS. 4-6, the first and second interlocking shaped surfaces 58 and 60 are three faceted surfaces which interlock with matching facets of the second interlocking shaped surface 60 of the outer housing 40. The three faceted surfaces may be generally U-shaped, so that the first and second interlocking shaped surfaces 58 and 60 serve to lock the squeegee 50 in a preferred position when the squeegee 50 is reeled in by the retractable reel 42. Therefore, the squeegee 50 may lock into place upon being released by the user, without any further action required by the user. While one embodiment of the interlocking shaped surfaces 58 and 60 is illustrated, alternative shapes may be devised by one skilled in the art, and these alternative shapes should be considered within the scope of the present invention.

As illustrated in FIGS. 4-6, the squeegee 50 may further include a V-shaped portion 62 adjacent the rubber cleaning edge 52. The V-shaped portion 62 is shaped to engage the goggles 12 to hold the squeegee 50 in place when not in use, to further prevent any movement of the eyewear cleaning device 10 during physical activities. The V-shaped portion 62 may be shaped to fit around the side of the goggles 12, such that the squeegee 50 is flush against the side of the goggles 12.

FIGS. 4-6 also illustrate a laterally extending handle portion 64 on the eyewear cleaning device 10. As illustrated in FIGS. 4-6, the laterally extending handle portion 64 extends from the squeegee 50 and provides a means by which the user may grip and manipulate the squeegee 50, even while wearing the goggles 12 and being engaged in athletic activity. The laterally extending handle portion 64 is shaped so that when the user grasps the squeegee 50 and pulls the squeegee 50 into an extended position to wipe the goggles 12 clean, the rubber cleaning edge 52 is correctly positioned for cleaning the goggles 12. The economic shape of the laterally extending handle portion 64 facilitates use of the eyewear cleaning device 10 during athletic activity. In an alternative embodiment, the handle portion 64 may have a different shape or decorative appearance, as long as it enables the user to grasp the squeegee 50 and clean the eyewear 12.

Figure 7A:
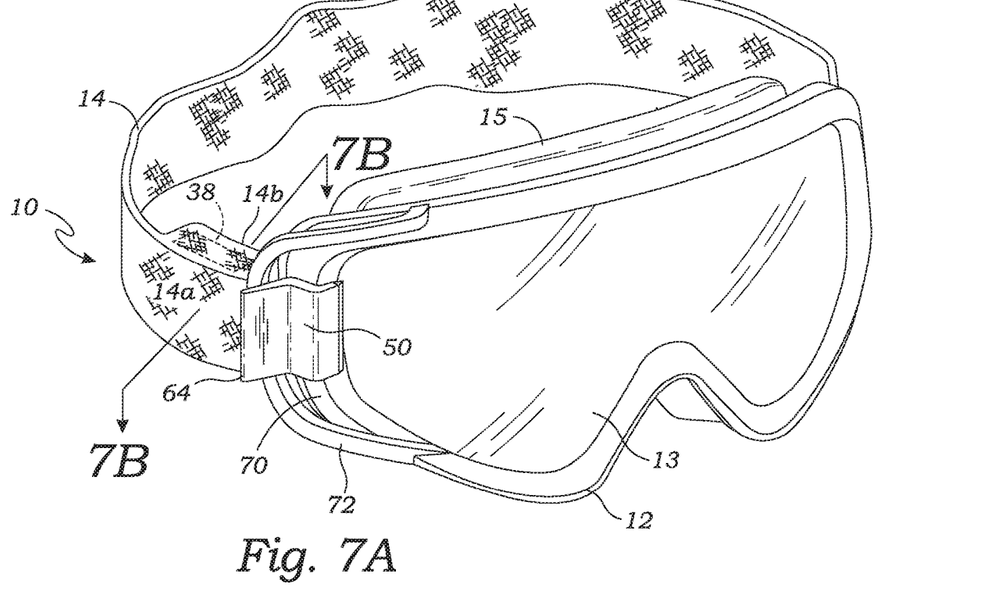
FIG. 7A is a perspective view of a third embodiment of the invention, wherein a retraction mechanism of the cleaning device is integrally mounted within a strap of the goggles.
Figure 7B:
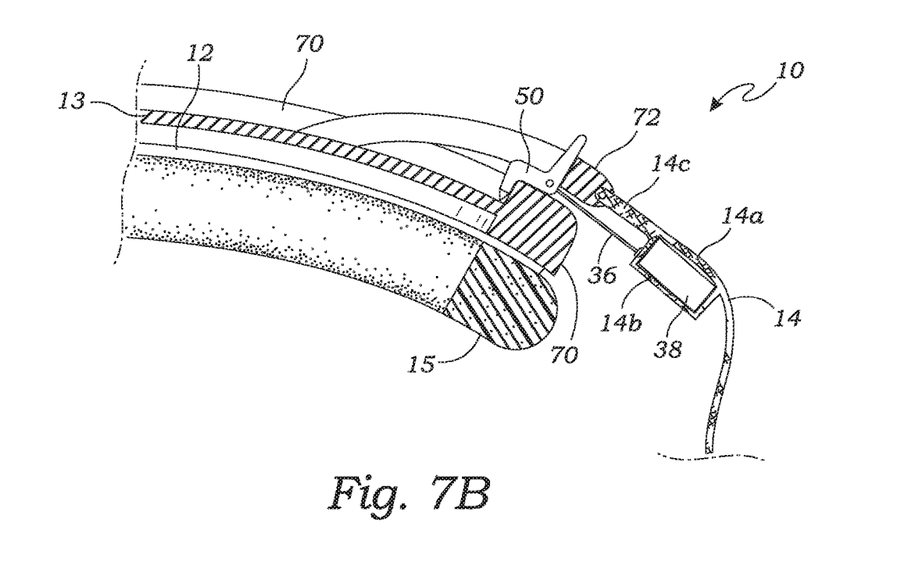
FIG. 7B is a sectional view thereof taken along line 7B-7B in FIG. 7A.

FIG. 7A is a perspective view of a third embodiment of the invention, wherein the retraction mechanism 38 of the cleaning device 10 is integrally mounted within a strap 14 of the goggles 12. FIG. 7B is a sectional view thereof taken along line 7B-7B in FIG. 7A. As shown in FIGS. 7A and 7B, the retraction mechanism 38 of this embodiment, which houses the retractable reel 42 (shown in FIG. 1, and discussed above) may be mounted within the strap 14, between an outer surface 14A and an inner surface 14B, such that it is adjacent an end 14C of the strap 14. In an alternative embodiment, it may be mounted on the outer surface 14A or the inner surface 14B, or in any other manner that may be devised by one skilled in the art. The retraction mechanism 38 may be constructed in any manner known to those skilled in the art, and may be fastened or otherwise fixedly mounted in any manner known to those skilled in the art, e.g., mechanically fastened (screws, staples, etc.), chemically secured (glue, adhesive, etc.) Or otherwise installed, by any method known to those skilled in the art (e.g., welded, etc.).

As shown in FIGS. 7A and 7B, the retraction mechanism 38 is mounted adjacent the end 14C of the strap 14, which is secured to a rigid frame 70 of the goggles 12, in this embodiment to a rigid loop 72 which forms an integral part of the frame 70. In this embodiment, the cord 36 extends between the loop 72 and the frame 70, so that the squeegee 50 is positioned adjacent the frame 70 and such that, in this embodiment, an edge 90 is adjacent a transparent lens 13. A gasket 15 (e.g., foam, rubber, silicone, etc.) Is mounted on the frame 70 around the perimeter of the lens 13 for sealing against the user's face.

Figure 8A:
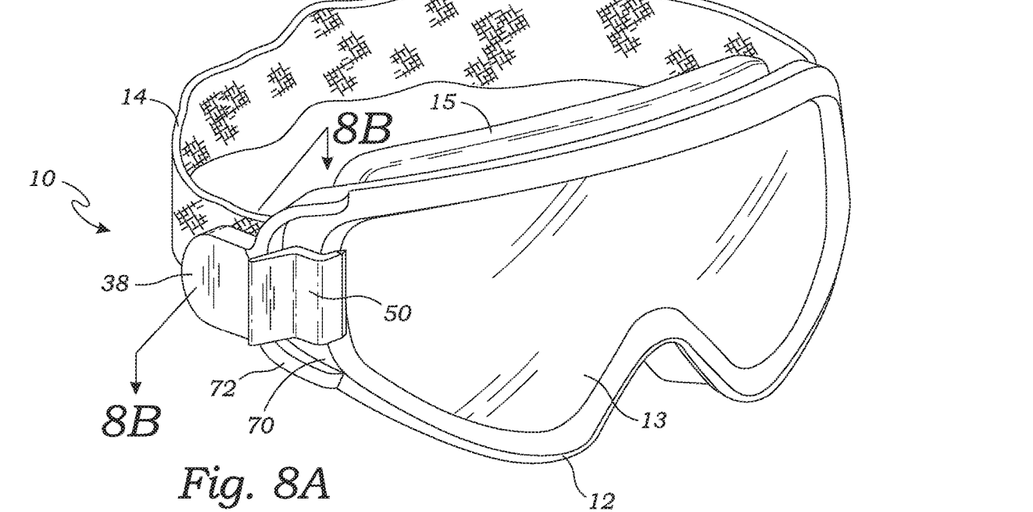
FIG. 8A is a perspective view of a fourth embodiment of the invention, wherein the retraction mechanism is integrally mounted on a frame of the goggles.
Figure 8B:
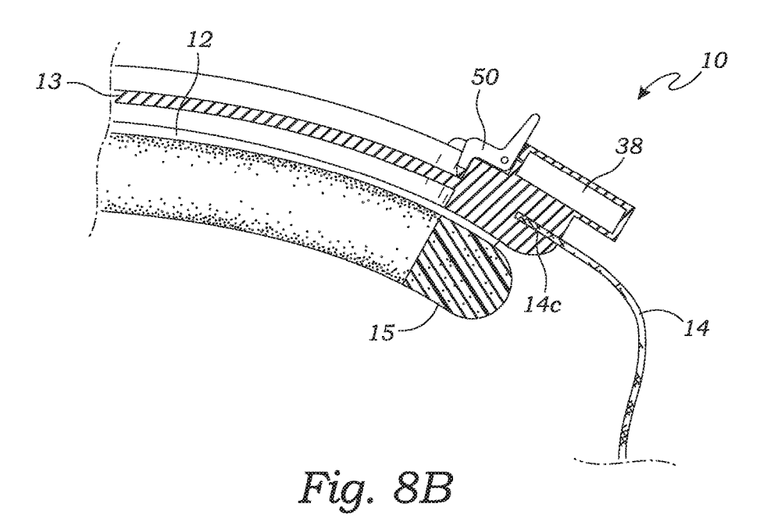
FIG. 8B is a sectional view thereof taken along line 8B-8B in FIG. 8A.

FIG. 8A is a perspective view of a fourth embodiment of the invention, wherein the retraction mechanism 38 of the cleaning device 10 is integrally mounted to the frame 70 of the goggles 12. FIG. 8B is a sectional view thereof taken along line 8B-8B in FIG. 8A. As shown in FIGS. 8A and 8B, the retraction mechanism 38 may be mounted in any suitable location, using any suitable mechanism, e.g., mechanically fastened (screws, staples, etc.), chemically secured (glue, adhesive, etc.) or otherwise installed, by any method known to those skilled in the art (e.g., integrally molded, welded, etc.).

Figure 9:
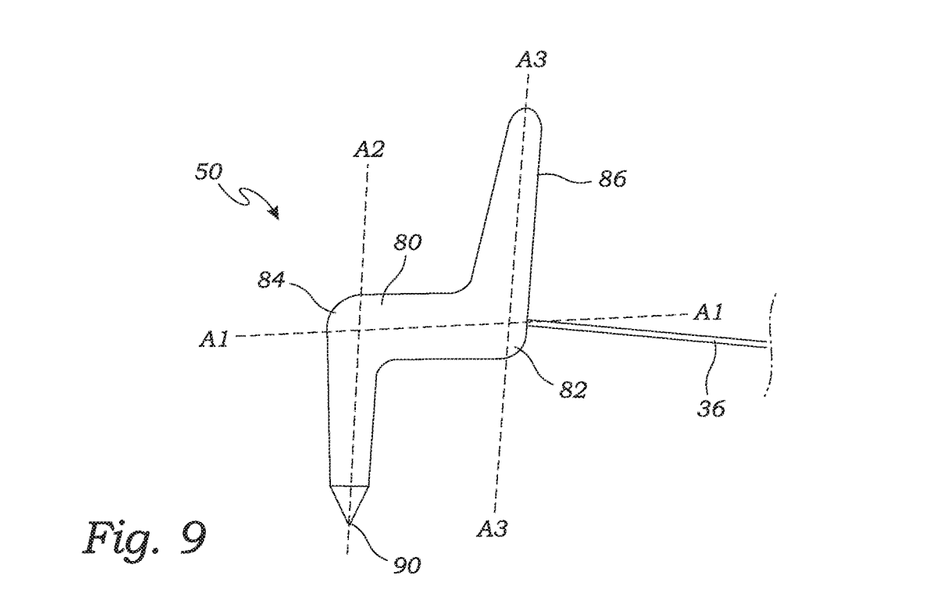
FIG. 9 is a side elevational view of a squeegee of FIG. 7A and 7B.
Figure 10:
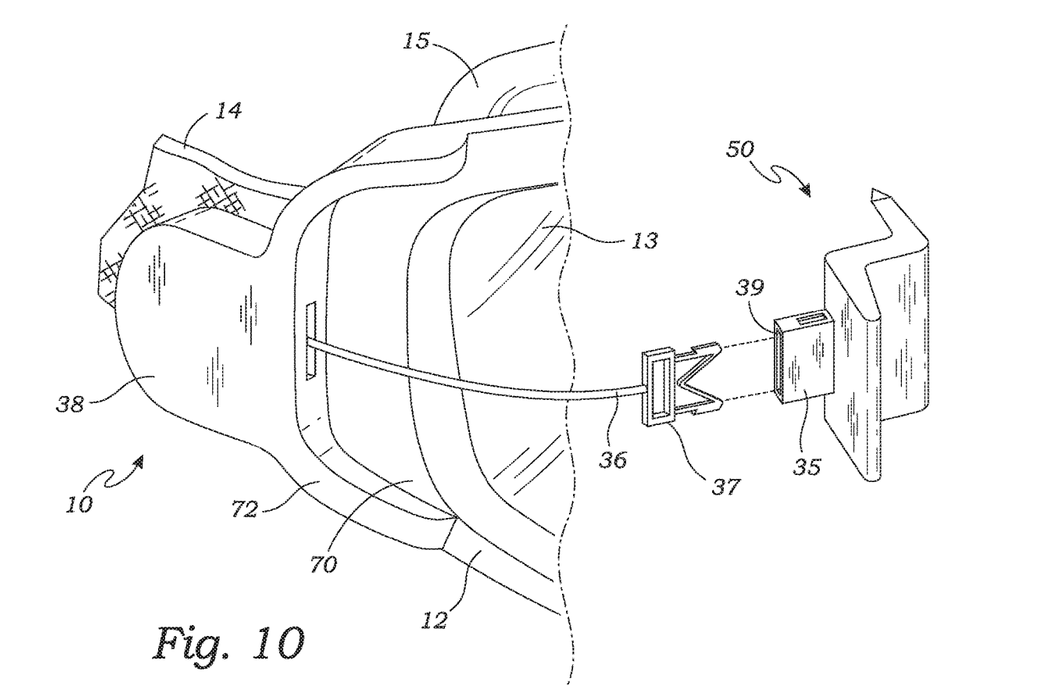
FIG. 10 is a close up perspective view of a portion of the goggles, with the squeegee shown in an exploded view to illustrate the attachment of the squeegee to a fastener of a cord of the retraction mechanism.

FIG. 9 is a side elevational view of an alternative embodiment of the squeegee 50. In this embodiment, the squeegee 50 includes a traverse body portion 80 that extends along a first axis A1 from a first end 82 to a second end 84. The first end 82 is attached to the cord 36, and a laterally extending handle portion 86 extends outwardly from the traverse body portion 80 at the first end 82. The laterally extending handle portion 86 extends outwardly on a third axis A3, which is approximately perpendicular to the first axis A1 of the traverse body portion 80. For purposes of this application, the term "approximately" is defined to mean +/−20%.

Similarly, a squeegee blade 88 extends outwardly from the traverse body portion 80 at the second point 84, in a direction opposite the laterally extending handle portion 86. The squeegee blade 88 extends outwardly on a second axis A2, which is approximately perpendicular to the first axis A1 of the traverse body portion 80. The squeegee blade 88 extends to an edge 90 that is suitable for wiping moisture, snow, etc., from the lens 13 of the goggles 12. This configuration enables the user to easily grasp the laterally extending handle portion 86, even while wearing gloves, and then use the squeegee blade 88 to wipe the goggles 12.

As used in this application, the words "a," "an," and "one" are defined to include one or more of the referenced item unless specifically stated otherwise. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application.

What is claimed is:

1. Goggles with an integral cleaning system, the goggles comprising:
   a lens mounted on a frame, the frame having a gasket adapted for seating against a user's face, and further comprising a strap adapted for securing the frame around the user's head;
   a retraction mechanism fixedly mounted on the strap;
   a squeegee for cleaning the lens of the goggles;
   a cord having a proximal end and a distal end, the proximal end being attached to the squeegee, and the distal end being operably attached to the retraction mechanism; and
   wherein the retraction mechanism is integrally mounted within the strap, adjacent an end of the strap adjacent the frame, between an outer surface and an inner surface of the strap.

2. The goggles of claim 1, wherein the squeegee includes a traverse body portion that extends along a first axis from a first end to a second end, wherein the first end is attached to the cord, and a laterally extending handle portion extends outwardly from the traverse body portion at the first end, and wherein the laterally extending handle portion extends outwardly on a third axis, which is approximately perpendicular to the first axis of the traverse body portion.

3. The goggles of claim 2, further comprising a squeegee blade that extends outwardly from the traverse body portion at a second point, in a direction opposite the laterally extending handle portion, and extends outwardly on a second axis which is approximately perpendicular to the first axis of the traverse body portion.

4. The goggles of claim 3, wherein the squeegee blade extends to an edge.

5. The goggles of claim 4, wherein the squeegee blade and the laterally extending handle portion are configured to enable the user to easily grasp the laterally extending handle portion and use the squeegee blade to clean the lens.

6. Goggles with an integral cleaning system, the goggles comprising:
- a lens mounted on a frame, the frame having a gasket adapted for seating against a user's face, and further comprising a strap adapted for securing the frame around the user's head;
- a retraction mechanism fixedly mounted on the strap;
- a squeegee for cleaning the lens of the goggles;
- a cord having a proximal end and a distal end, the proximal end being attached to the squeegee, and the distal end being operably attached to the retraction mechanism;
- wherein the retraction mechanism is integrally mounted within the strap, adjacent an end of the strap adjacent the frame, between an outer surface and an inner surface of the strap, wherein the strap, is secured to a rigid loop, and the rigid loop extends from and forms an integral part of the frame; and
- wherein the cord extends between the rigid loop and the frame, so that the squeegee is positioned adjacent the frame.

* * * * *